Figure 1:
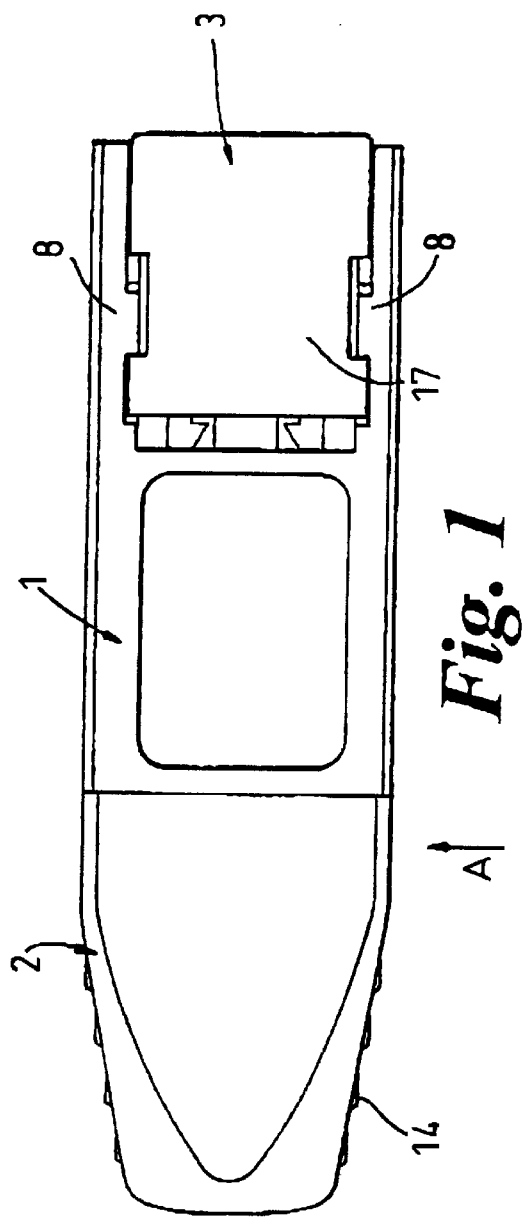

United States Patent [19]
Weekes

[11] Patent Number: 6,090,124
[45] Date of Patent: Jul. 18, 2000

[54] RELATING TO SKIN PRICKERS

[75] Inventor: Stuart Weekes, Littlemore, United Kingdom

[73] Assignee: Owen Mumford Limited, Oxford, United Kingdom

[21] Appl. No.: 09/242,324

[22] PCT Filed: Aug. 12, 1997

[86] PCT No.: PCT/GB97/02165

§ 371 Date: Mar. 24, 1999

§ 102(e) Date: Mar. 24, 1999

[87] PCT Pub. No.: WO98/06331

PCT Pub. Date: Feb. 19, 1998

[30] Foreign Application Priority Data

Aug. 13, 1996 [GB] United Kingdom ............... 9616953

[51] Int. Cl.[7] .................................................. A61B 17/14
[52] U.S. Cl. ........................................................ 606/182
[58] Field of Search ................................. 606/181, 182, 606/184, 185, 189, 167

[56] References Cited

U.S. PATENT DOCUMENTS

| 4,416,279 | 11/1983 | Lindner et al. |
| 5,464,418 | 11/1995 | Schraga |
| 5,540,709 | 7/1996 | Ramel ..................................... 606/182 |

FOREIGN PATENT DOCUMENTS 0 293 092  11/1988  European Pat. Off. .

*Primary Examiner*—Michael Buiz
*Assistant Examiner*—Vy Q. Bui
*Attorney, Agent, or Firm*—Young & Thompson

[57] ABSTRACT

A skin pricker has a body (1) with a spring-loaded lancet holder (4) with a forward facing socket (20) to receive the rear end of a lancet. The socket (20) is radially expandable/compressible and the spring-loading is a coil spring (5) part of which embraces the socket and tends to close it up. This allows lancets of slightly varying diameters to be firmly held. The pricker is primed by pressing a lancet into the socket (20), which urges the holder (4) back to be releasably held by a trigger mechanism (3, 9).

11 Claims, 2 Drawing Sheets

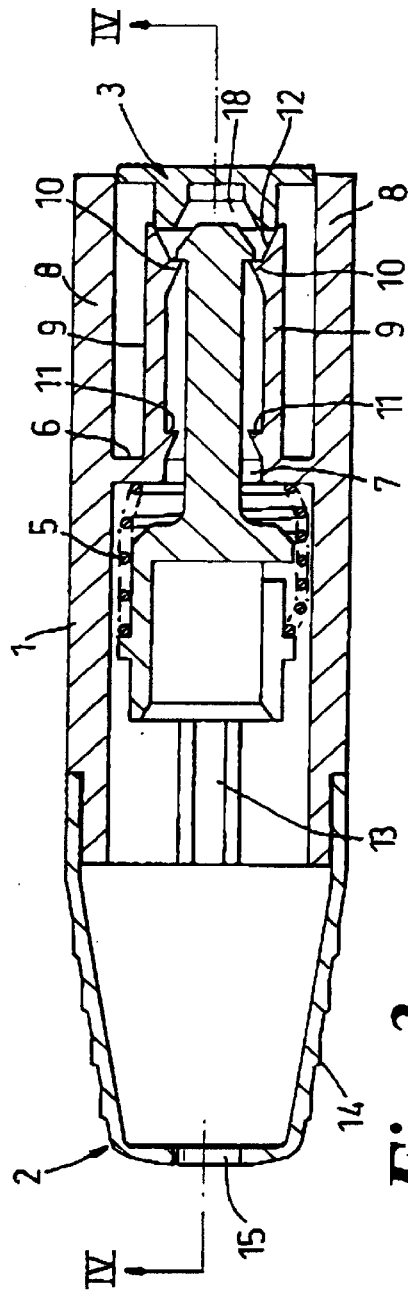
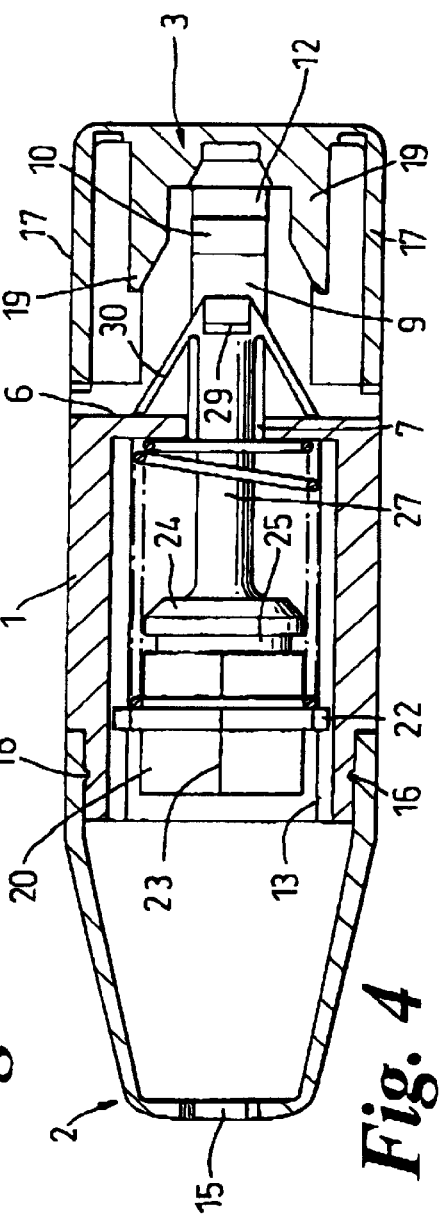
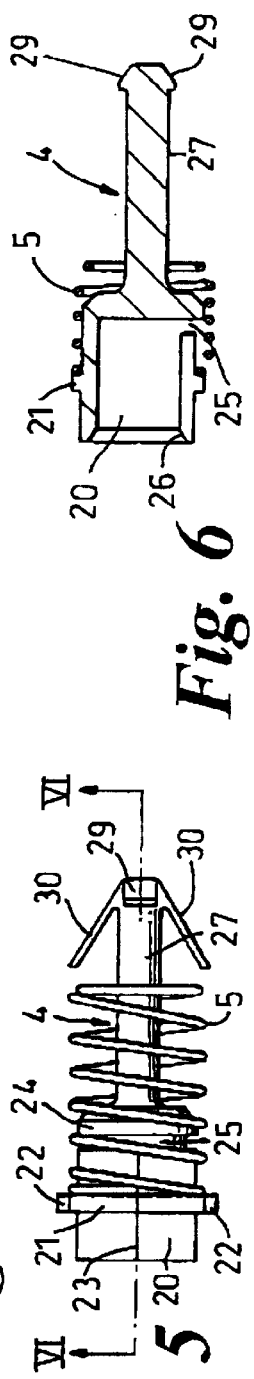
Fig. 3
Fig. 4
Fig. 5
Fig. 6

RELATING TO SKIN PRICKERS

This invention relates to skin prickers.

A small blood sample is required for analysis or testing in many medical situations. Often, it is left to the patient to draw his own sample and carry out his own test on home use equipment, and many lancet devices have been devised to make the procedure simple, safe and as painless as possible. Commonly, there is a firing mechanism which can be used many times, but at each use it has to be loaded with a fresh lancet, which is thrown away once the sample has been taken. There are obvious dangers in reusing a lancet.

To be throwaway items, the lancets have to be cheap. The usual form is a needle encased in a generally cylindrical plastics body, leaving just the tip exposed when an integrally moulded tear-off cap is removed. Such lancets, although they may conform to this general pattern, are not uniformly sized, and there can even be differences in a batch from the same manufacturer.

A common way of holding the lancet in the firing device is to press its rear end into a socket at the forward end of a spring loaded holder which is released by a trigger mechanism. The press fit should hold the lancet secure during use, but due to the variations in size mentioned above, this is not always the case. Sometimes the lancets are loose, and sometimes they are too large to be pressed into the sockets, at least not without damage or permanent distension.

It is the aim of this invention to provide a simple skin pricker which can accommodate to variations in lancet size.

According to the present invention there is provided a skin pricker having a body containing a spring loaded lancet carrier releasable from a rearward position to cause the lancet tip to project momentarily from the leading end of the body, wherein the lancet carrier has a forwardly open socket into which the rear end of a lancet is plugged, and wherein the spring loading is a coil spring part of which embraces the socket normally to constrict it to a minimum diameter but which allows the socket to expand to receive the rear end of a lancet with a diameter greater than said minimum.

Thus, a lancet can be pressed into the socket and it will expand as necessary to accommodate it, the spring ensuring that it retains a firm grip. The mouth of the socket may be flared to ease entry and generate the initial expansion.

In one preferred form the socket has a longitudinal split from mouth to base, and at the base on either side of this split the socket wall is cut away circumferentially so that there are two wings which can spread to widen the split. There may be more than one such split around the circumference of the socket.

The lancet carrier preferably has a portion extending rearwardly of the socket with a detent for retention by a release mechanism when the carrier is moved to its rearward position. This release mechanism may include two rearwardly projecting figures internal of the body and flanking said portion to co-operate with opposed detents, and a pressure element at the rear of the body to co-operate with the fingers and, when pressed, to spread them to disengage the detents.

The lancet carrier will generally be of moulded plastics, in which case said portion may have forwardly and outwardly projecting fingers which form spring elements that co-operate with an abutment internal of the body to cushion the end of the forward stroke of the lancet carrier and promote the return of the lancet tip within the body. The rear end of the coil spring conveniently acts against the forward side of said abutment.

Figure 2:
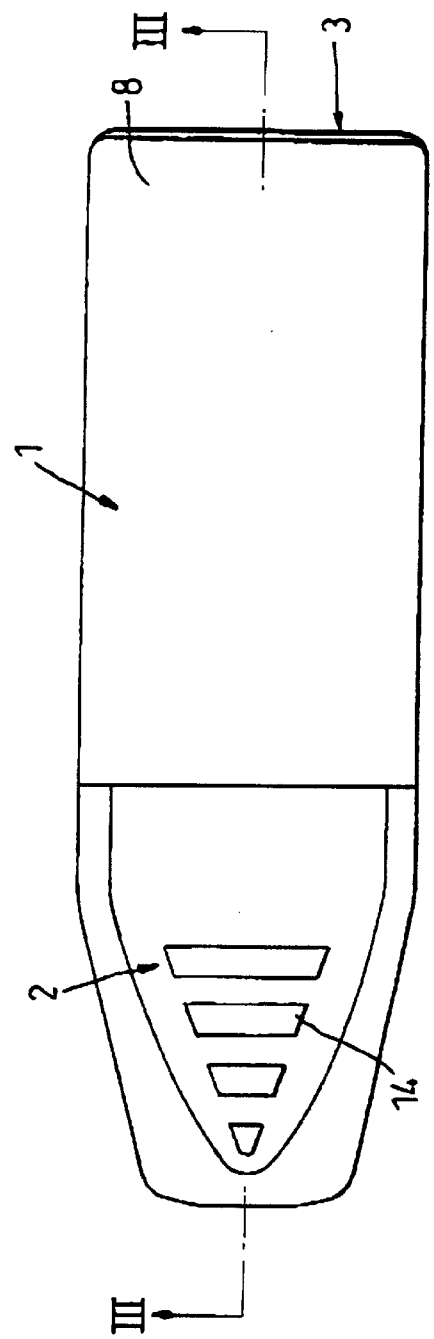

For a better understanding of this invention, one embodiment will now be described, by way of example, with reference to the accompanying drawing, in which:

FIG. 1 is a side view of a skin pricker,

FIG. 2 is another side view of the skin pricker, seen in the direction A of FIG. 1, FIG. 3 is a longitudinal section of the pricker on the line III—III of FIG. 2, before firing, FIG. 4 is a longitudinal section of the pricker, apart form the lancet holder which is seen in side view, on the line IV—IV of FIG. 3, but after firing, FIG. 5 is a side view of the lancet holder and spring assembly, and FIG. 6 is a longitudinal section of that assembly on the line VI—VI of FIG. 5.

The main components of the skin pricker are a generally box section body 1, a cap 2 which fits the forward end of the body, a pressure member 3 which fits the rear end of the body, a lancet holder 4 within the body, and a spring 5.

The body 1 is of box section from its leading end to a bulkhead 6 having a central aperture 7. To the rear of that two opposed faces extend in parallel wings 8 while the other two faces stop short at the bulkhead 6. On either side of the aperture 7 two fingers 9 extend rearwardly parallel to and inside the wings 8, and on the inside these fingers have teeth 10 near their rear ends and teeth 11 adjacent their roots. Beyond the teeth 10, the inside surfaces 12 of the fingers flare outwardly. Forward of the bulkhead 6, two opposed inside faces of the body 1 have longitudinal ribs forming guide channels 13.

The cap 2 is externally ribbed at 14 for grip and has an aperture 15 at its leading end through which the tip of a lancet will be projected. It is a close fit over an external rebate at the leading end of the body 1, and internally two opposite sides of the cap 2 have ribs 16 which snap into grooves in that rebate. The cap is therefore secure enough for use, but can be pulled off and pressed on when exchanging lancets.

The pressure member 3 is generally U-shaped and its side limbs 17 substantially fill the spaces between the edges of the wings 8, which are stepped positively to retain the pressure member 3 to the body, but allowing it limited longitudinal movement. Internally, the base of the member 3 has a cup 18 which can freely receive the rear end of the lancet holder 4 and whose rim co-operates with the flared surfaces 12 of the fingers 9. At opposite sides, the cup is extended by two forwardly projecting fingers 19.

The lancet holder 4, which can be seen separately, with its spring, in FIGS. 5 and 6 is approximately of wine glass shape. At the forward end, the "bowl" is a generally cylindrical socket 20 provided externally at about its mid-length with a circumferential rib 21 having diametrically opposed projecting lugs 22. These guide the holder 4 by engaging in the channels 13. The socket has a longitudinal split 23 from mouth to base, and adjacent the base 24 the walls are circumferentially cut away at 25 in both directions, forming wings on either side of the split 23. The mouth of the socket is internally flared as shown at 26 in FIG. 6.

The stem 27 terminates at the rear end in two opposed lateral teeth 29 alternating around the stem with two opposed fingers 30 extending forwardly and outwardly. The holder 4 is of plastics material and the fingers are thin enough to have resilience and act as springs.

The main coil spring 5 encircles the stem 28 and the rear portion of the socket 20, to bear against the rib 21. But it does more than just bear against this rib; its final turn squeezes the socket normally to keep the split 23 closed up. This assembly is then entered into the body 1 from the forward end, and the fingers 30 close up to the stem 28 to allow the rear end to squeeze through the aperture 7. The fingers 30 then spread out again and the spring 5 is left bearing against the forward side of the bulkhead 6. The teeth 29 can snap past the teeth 11 and 10 to the position of FIG. 3, where the device is primed. This final motion may be achieved when plugging the rear end of a lancet into the socket 19, which spreads as necessary to receive the lancet. The lancet will be of the usual generally cylindrical form, with a plastics body encasing a steel needle. Initial entry is eased by the flare 26, while the coil spring 5 ensures that the grip is firm. The fingers 19, by co-operating with the fingers 30, keep the lancet holder from tilting in the plane of FIG. 4, while any tendency to tilt at right angles to this is prevented by the fingers 9.

For firing the device, the pressure member 3 is urged forwards, and the cup 18 spreads the fingers 9 by acting on the surfaces 12. The teeth 10 then release the teeth 29 and the lancet holder 4 shoots forward briefly to project the needle tip. The ends of the fingers 30 hit the bulkhead 6 and spread. A definite limit on the forward movement is imposed by the teeth 29 meeting the teeth 11, which will not have been parted to any significant degree by the pressure member 3. The fingers 30 then recover to pull the holder 4 back to retract the needle tip inwards from the aperture 15. The cap 2 can then be removed and the lancet unplugged simply by pulling it away from the socket 20. The device is then ready to receive a fresh lancet.

What is claimed is:

1. A skin pricker having a body (1), a lancet carrier (4) within the body (1) and having a forwardly open socket (20) into which the rear end of a disposable lancet may be plugged, and a coil spring (5) and a release mechanism (3, 9, 10) arranged for projecting the lancet carrier (4) forwards momentarily to project the tip of a fitted lancet from the leading end of the body (1), characterised in that part of the coil spring (5) embraces the socket (20) and, without a lancet fitted, constricts the socket to a minimum diameter, but which allows the socket to expand to receive the rear end of a lancet with a diameter greater than said minimum diameter.

2. A skin pricker as claimed in claim 1, characterised in that the mouth of the socket (20) is flared (26) to ease entry and generate the initial expansion.

3. A skin pricker as claimed in claim 1, characterised in that the socket (20) has at least one longitudinal split (23) from mouth to base (24).

4. A skin pricker as claimed in claim 3, characterised in that at the base (24) on either side of the at least split (23) the socket wall is cut away (25) circumferentially so that there are two wings which can spread to widen the split.

5. A skin pricker as claimed in claim 1, characterised in that the lancet carrier (4) has a portion (27) extending rearwardly of the socket (20) with a detent (29) for retention by the release mechanism (3, 9, 10) when the carrier (4) is moved to its rearward position.

6. A skin pricker as claimed in claim 5, characterised in that the release mechanism includes two rearwardly projecting fingers (9) internal of the body (1) and flanking said portion (27) to co-operate with opposed detents (29), and a pressure element (3) at the rear of the body to co-operate with the fingers (9) and, when pressed, to spread them to disengage the detents (29).

7. A skin pricker as claimed in claim 5, characterised in that the lancet carrier (4) is of moulded plastics and said portion (27) has forwardly and outwardly projecting fingers (30) which form spring elements that co-operate with an abutment (6) internal of the body (1) to cushion the end of the forward stroke of the lancet carrier (4) and promote the return of the lancet tip within the body.

8. A skin pricker as claimed in claim 7, characterised in that the rear end of the coil spring (5) acts against the forward side of said abutment (6).

9. A skin pricker as claimed in claim 2, characterized in that the socket (20) has at least one longitudinal split (23) from mouth to base (24).

10. A skin pricker as claimed in claim 6, characterized in that the lancet carrier (4) is of moulded plastics and said portion (27) has forwardly and outwardly projecting fingers (30) which form spring elements that co-operate with an abutment (6) internal of the body (1) to cushion the end of the forward stroke of the lancet carrier (4) and promote the return of the lancet tip within the body.

11. A skin pricker as claimed in claim 10, characterized in that the rear end of the coil spring (5) acts against the forward side of said abutment (6).

* * * * *